United States Patent
Chiang et al.

(10) Patent No.: US 9,867,973 B2
(45) Date of Patent: Jan. 16, 2018

(54) SKIN ANTISEPTIC APPLICATOR AND METHODS OF MAKING AND USING THE SAME

(71) Applicant: Medline Industries, Inc., Northfield, IL (US)

(72) Inventors: Casper W. Chiang, Danville, CA (US); Benjamin Ma, Pleasanton, CA (US); Bradley L. Kirsch, Pleasanton, CA (US)

(73) Assignee: Medline Industries, Inc., Northfield, IL (US)

( * ) Notice: Subject to any disclaimer, the term of this patent is extended or adjusted under 35 U.S.C. 154(b) by 937 days.

(21) Appl. No.: 14/261,360

(22) Filed: Apr. 24, 2014

(65) Prior Publication Data

US 2014/0371694 A1    Dec. 18, 2014

Related U.S. Application Data

(60) Provisional application No. 61/836,052, filed on Jun. 17, 2013.

(51) Int. Cl.
*A61M 35/00* (2006.01)
*A61F 13/40* (2006.01)
(Continued)

(52) U.S. Cl.
CPC ........... *A61M 35/006* (2013.01); *B29C 49/04* (2013.01); *B29K 2101/12* (2013.01);
(Continued)

(58) Field of Classification Search
CPC ... A61M 35/006; A61M 35/00; A61M 35/003
(Continued)

(56) References Cited

U.S. PATENT DOCUMENTS 2,318,380 A    5/1943    Davis et al.
3,271,810 A    9/1966    Raffe
(Continued)

FOREIGN PATENT DOCUMENTS

CA    2796699    5/2014
CN    102993056 A    3/2013
(Continued)

OTHER PUBLICATIONS

Gershenfeld, Louis; 'Povidone-Iodine as a Sporicide', American Journal of Pharmacy, Philadelphia, Pa., vol. 134, Mar. 1962, p. 78-81, P.
(Continued)

*Primary Examiner* — Susan Su
(74) *Attorney, Agent, or Firm* — Fitch, Even, Tabin & Flannery LLP

(57) ABSTRACT

The invention relates to applicators for applying a solution or other composition (e.g., an antiseptic composition) to skin of a patient. The applicator may include a container body having a proximal end, a distal end, and a frangible member disposed at the distal end of the body. The applicator includes a first position where the container body and frangible member are a unitary piece (e.g., blow molded as a single piece), and a second position when the frangible member is rotated relative to the body to irreversibly break a weak point therebetween, releasing the composition in the hollow body through an opening. A porous applicator head may be positioned adjacent the distal end of the body and frangible member, so that the composition flows out the body, through the opening, and onto the head. The applicator may be formed in a blow-fill-seal process for improved sterility and ease of manufacture.

28 Claims, 11 Drawing Sheets

(51) Int. Cl.
  *B29C 49/04* (2006.01)
  *B29K 101/12* (2006.01)
  *B29K 509/00* (2006.01)
  *B29L 31/00* (2006.01)

(52) U.S. Cl.
  CPC .. *B29K 2509/00* (2013.01); *B29K 2995/0029* (2013.01); *B29L 2031/712* (2013.01); *B29L 2031/7158* (2013.01); *B29L 2031/7546* (2013.01)

(58) Field of Classification Search
  USPC .......................................... 604/1–3, 289, 310
  See application file for complete search history.

(56) References Cited

U.S. PATENT DOCUMENTS

| | | | |
|---|---|---|---|
| 3,618,283 A | 11/1971 | Moore et al. | |
| 3,725,003 A | 4/1973 | Moore | |
| 3,847,151 A * | 11/1974 | D'Alessandro | A47L 17/00 15/244.1 |
| 3,855,380 A | 12/1974 | Cleevely | |
| 3,857,677 A | 12/1974 | Moore | |
| 3,862,242 A | 1/1975 | Terrell | |
| 3,876,314 A | 4/1975 | Nehring | |
| D245,221 S | 8/1977 | Hoyt | |
| 4,050,894 A | 9/1977 | Genis | |
| 4,101,618 A | 7/1978 | Aoki | |
| 4,106,654 A | 8/1978 | Jones | |
| 4,169,123 A | 9/1979 | Moore et al. | |
| 4,438,011 A | 3/1984 | Howes | |
| 4,510,115 A | 4/1985 | Gokcen | |
| 4,646,629 A | 3/1987 | Creed et al. | |
| 4,671,763 A | 6/1987 | Weiler | |
| 4,707,966 A | 11/1987 | Weiler | |
| 4,753,591 A | 6/1988 | Maes | |
| 4,856,136 A | 8/1989 | Janssen | |
| 4,925,327 A | 5/1990 | Wirt | |
| 4,948,356 A | 8/1990 | Dundas | |
| 4,957,385 A | 9/1990 | Weinstein | |
| 4,988,399 A | 1/1991 | Watson | |
| 5,011,648 A | 4/1991 | Garver | |
| 5,054,267 A | 10/1991 | Dundas | |
| 5,069,856 A | 12/1991 | Holoubek | |
| 5,098,291 A | 3/1992 | Curtis et al. | |
| 5,203,379 A | 4/1993 | Holoubek | |
| 5,238,148 A | 8/1993 | Holoubek | |
| 5,288,159 A | 2/1994 | Wirt | |
| 5,326,603 A | 7/1994 | Van Dyke | |
| 5,341,538 A | 8/1994 | Banome | |
| 5,357,636 A | 10/1994 | Dresdner, Jr. et al. | |
| 5,538,353 A | 7/1996 | DeHavilland | |
| 5,573,800 A | 11/1996 | Wilhoit | |
| 5,573,801 A | 11/1996 | Wilhoit | |
| D377,978 S | 2/1997 | Haber | |
| D386,849 S | 11/1997 | DeHavilland | |
| 5,690,958 A | 11/1997 | McGrath | |
| 5,752,363 A | 5/1998 | Edwards | |
| 5,772,346 A | 6/1998 | Edwards | |
| D396,911 S | 8/1998 | DeHavilland | |
| 5,901,865 A | 5/1999 | Weiler | |
| 5,908,124 A | 6/1999 | Klauke | |
| 5,918,783 A | 7/1999 | Kieras | |
| D414,688 S | 10/1999 | Loeb | |
| 6,129,880 A | 10/2000 | Kieras | |
| 6,139,794 A | 10/2000 | Asgharian et al. | |
| 6,299,377 B1 | 10/2001 | Emerit | |
| 6,488,665 B1 | 12/2002 | Severin et al. | |
| 6,516,947 B1 * | 2/2003 | Van Dyke | A45D 34/042 206/361 |
| 6,533,484 B1 | 3/2003 | Osei | |
| 6,536,975 B1 | 3/2003 | Tufts | |
| 6,595,940 B1 | 7/2003 | D'Alessio et al. | |
| 6,595,969 B1 * | 7/2003 | Emerit | A61M 35/006 401/266 |
| 6,673,301 B2 | 1/2004 | Cargile | |
| 6,729,786 B1 | 5/2004 | Tufts | |
| 6,852,267 B1 | 2/2005 | Keller | |
| 6,991,393 B2 | 1/2006 | Tufts | |
| 6,991,394 B2 | 1/2006 | Tufts | |
| 7,182,536 B2 | 2/2007 | Tufts | |
| 7,188,750 B2 | 3/2007 | Vogel | |
| 7,241,065 B2 | 7/2007 | Tufts | |
| 7,261,701 B2 | 8/2007 | Davis | |
| 7,306,390 B2 | 12/2007 | Quintero | |
| 7,422,388 B2 | 9/2008 | Tufts | |
| 7,562,796 B2 * | 7/2009 | Zahn | A61J 1/067 215/11.4 |
| 7,614,811 B2 | 11/2009 | Kaufman | |
| 7,637,679 B2 | 12/2009 | May et al. | |
| 7,824,122 B2 | 11/2010 | Flores | |
| 7,866,514 B1 | 1/2011 | Hansen | |
| 7,866,907 B2 | 1/2011 | Cable | |
| 7,868,016 B2 | 1/2011 | Singh et al. | |
| 7,946,779 B2 | 5/2011 | Kaufman | |
| 7,993,066 B2 | 8/2011 | Flores | |
| 8,047,394 B2 | 11/2011 | Hansen | |
| 8,062,649 B2 | 11/2011 | Asmus et al. | |
| 8,083,425 B2 | 12/2011 | Kaufman | |
| 8,105,306 B2 | 1/2012 | Davis | |
| 8,110,144 B2 | 2/2012 | Morales | |
| 8,118,508 B2 | 2/2012 | Goodman et al. | |
| 8,118,766 B2 | 2/2012 | Davis | |
| 8,186,897 B2 | 5/2012 | Kaufman | |
| 8,215,859 B2 | 7/2012 | Kaufman | |
| 8,338,491 B2 | 12/2012 | Asmus | |
| 8,343,525 B2 | 1/2013 | Davis | |
| 8,383,038 B2 | 2/2013 | Kitano | |
| D684,259 S | 6/2013 | Mehta | |
| 8,511,923 B2 | 8/2013 | Kaufman | |
| 8,550,737 B2 | 10/2013 | Ruiz | |
| 8,556,529 B2 | 10/2013 | Law | |
| 8,591,130 B2 | 11/2013 | Koptis | |
| 8,685,309 B2 | 4/2014 | Klofta | |
| 8,734,923 B2 | 5/2014 | Shi | |
| 8,833,576 B2 | 9/2014 | Fontana | |
| 8,858,484 B2 | 10/2014 | Casey | |
| 8,911,771 B2 | 12/2014 | Vanek | |
| 8,979,785 B2 | 3/2015 | Korogi | |
| 9,283,364 B2 | 3/2016 | Lockwood | |
| 9,314,956 B2 | 4/2016 | Porter | |
| 2001/0027301 A1 * | 10/2001 | Lau | A61J 1/067 604/310 |
| 2002/0028102 A1 | 3/2002 | Ozu | |
| 2003/0049069 A1 * | 3/2003 | Osei | A61M 35/003 401/205 |
| 2004/0068218 A1 | 4/2004 | Davis | |
| 2004/0120849 A1 | 6/2004 | Stewart et al. | |
| 2004/0170780 A1 | 9/2004 | Giraud | |
| 2004/0240927 A1 * | 12/2004 | Hoang | A61M 35/006 401/133 |
| 2004/0253039 A1 | 12/2004 | Stenton | |
| 2004/0267182 A1 | 12/2004 | Davis | |
| 2005/0067414 A1 | 3/2005 | Lipson | |
| 2005/0262811 A1 | 12/2005 | Mohiuddin | |
| 2005/0267423 A1 | 12/2005 | Johnson et al. | |
| 2006/0210746 A1 | 9/2006 | Shi | |
| 2006/0247568 A1 * | 11/2006 | Stenton | A61M 35/003 604/3 |
| 2007/0178051 A1 | 8/2007 | Pruitt et al. | |
| 2007/0253909 A1 | 11/2007 | Magallon | |
| 2007/0254854 A1 | 11/2007 | Magallon | |
| 2007/0262096 A1 * | 11/2007 | Gaynes | A61F 9/0008 222/420 |
| 2007/0276312 A1 * | 11/2007 | Davis | A61M 35/006 604/3 |
| 2007/0286668 A1 | 12/2007 | Kaufman | |
| 2008/0033367 A1 | 2/2008 | Haury | |
| 2008/0139519 A1 | 6/2008 | Ashley et al. | |
| 2009/0036863 A1 | 2/2009 | Smith | |
| 2009/0200191 A1 | 8/2009 | Matsuda | |
| 2009/0232580 A1 * | 9/2009 | Castel | A45D 34/04 401/41 |

(56) References Cited

U.S. PATENT DOCUMENTS

| | | |
|---|---|---|
| 2010/0133295 A1 | 6/2010 | Chan |
| 2010/0225030 A1 | 9/2010 | Hirdina |
| 2010/0232732 A1 | 9/2010 | Matthiesen |
| 2010/0286637 A1* | 11/2010 | Cable, Jr. ............ A61M 35/003 604/310 |
| 2011/0142527 A1 | 6/2011 | Kaufman |
| 2011/0177193 A1 | 7/2011 | Linke |
| 2011/0248045 A1 | 10/2011 | Harris |
| 2011/0264059 A1 | 10/2011 | Klofta |
| 2011/0319842 A1 | 12/2011 | McDonald |
| 2012/0003029 A1 | 1/2012 | Guzman et al. |
| 2012/0028651 A1 | 2/2012 | Hines et al. |
| 2012/0031870 A1 | 2/2012 | Porter |
| 2012/0051829 A1 | 3/2012 | Margoosian |
| 2012/0098165 A1 | 4/2012 | Baumgarte |
| 2012/0141186 A1 | 6/2012 | McDonald |
| 2012/0163898 A1 | 6/2012 | Kaufman |
| 2012/0184929 A1 | 7/2012 | Davis |
| 2012/0193838 A1 | 8/2012 | Bock |
| 2012/0237452 A1 | 9/2012 | Colomer |
| 2012/0238635 A1 | 9/2012 | Colomer |
| 2012/0251219 A1 | 10/2012 | Kaufman |
| 2012/0267832 A1 | 10/2012 | Zocher |
| 2013/0028651 A1* | 1/2013 | Kaufman ............ A61M 35/003 401/133 |
| 2013/0156486 A1 | 6/2013 | Guzman |
| 2013/0156640 A1 | 6/2013 | Kohler et al. |
| 2013/0193008 A1 | 8/2013 | Reyhan et al. |
| 2013/0336705 A1 | 12/2013 | Kaufman |
| 2014/0057864 A1 | 2/2014 | Kim |
| 2014/0322072 A1 | 10/2014 | Margoosian et al. |
| 2014/0371694 A1 | 12/2014 | Chiang |
| 2016/0129621 A1 | 5/2016 | Lisch |
| 2016/0207242 A1 | 7/2016 | Ferrari |
| 2016/0236820 A1 | 8/2016 | Paauwe |

FOREIGN PATENT DOCUMENTS

| | | |
|---|---|---|
| CN | 103202827 A | 7/2013 |
| WO | WO9922801 A1 | 5/1999 |
| WO | 2005099808 A1 | 10/2005 |
| WO | WO2005099808 A1 | 10/2005 |

OTHER PUBLICATIONS

Dictionary.reference.com; definition of 'Bottle'; http://dictionary.reference.com/browse/bottle?s=t; accessed Jul. 20, 2015.

Small, Heather. et al., "Efficacy of adding 2 percent (w/v) chlorhexidine gluconate to 70 percent (v/v) isopropyl alcohol for skin disinfection prior to peripheral venous cannulation"; Infection Control and Hospital Epidemiology, vol. 29, pp. 963-965; abstract, title (2008).

PCT International Search Report, PCT/US15/10465, dated Apr. 13, 2015.

U.S. Appl. No. 14/198,457; dated Sep. 26, 2014 NonFinal Office Action, Inventor: Satish Degala et al.

U.S. Appl. No. 14/198,457; dated Mar. 12, 2015 NonFinal Office Action, Inventor: Satish Degala et al.

U.S. Appl. No. 14/150,488; dated May 5, 2015 NonFinal Office Action, Inventor: Satish Degala et al.

U.S. Appl. No. 13/962,317; dated Jul. 8, 2015 NonFinal Office Action, Inventor: Razmmik Margoosian.

\* cited by examiner

SKIN ANTISEPTIC APPLICATOR AND METHODS OF MAKING AND USING THE SAME

CROSS-REFERENCE TO RELATED APPLICATIONS

The present application claims the benefit of U.S. Provisional Patent Application Ser. No. 61/836,052, filed Jun. 17, 2013, the disclosure of which is incorporated by reference in its entirety.

BACKGROUND OF THE INVENTION

1. The Field of the Invention

The present invention is directed to skin antiseptic composition applicators, particularly to skin antiseptic composition applicators that include one or more antimicrobial (e.g., antiseptic) materials in a single use applicator. Typically such skin antiseptic applicators are used in preparation for surgery to decolonize the skin prior to surgery and provide some protection to the patient's skin after surgery to prevent infection and aid in the healing process.

2. Description of Related Art

Antiseptic preparation of patient's skin for surgery conventionally includes a two to ten minute scrubbing of the affected area with an antiseptic soap solution followed by the application of a water-soluble antiseptic composition.

These compositions are generally applied with saturated sponges that are attached to a blade or held with forceps. These sponges are often saturated by soaking them in an open pan of antiseptic composition. Sometimes, sponges with attached handles are provided in a plastic or aluminum foil laminate pouch containing enough liquid to saturate the sponge. In some products the sponges are supplied dry in a sterile kit with the antiseptic composition provided in relatively thin walled 4 oz. plastic bottles.

While inexpensive, these techniques are messy and offer little control over inadvertent dripping of the composition into areas where it is undesired. Since many of the available compositions contain active ingredients such as alcohol, iodine or chlorhexidine gluconate, dripping or pooling of such compositions at unintended locations can be irritating when left in contact with the skin. As such, good control over the application has long been desirable, although not always provided.

Skin antiseptic applicator devices have been developed in an attempt to prevent composition dripping associated with the above techniques, and to reduce the time required for application of the antiseptic composition. In particular, the ChloraPrep® products commercially available from Care-Fusion and the DuraPrep® products commercially available from 3M have enjoyed commercial success by providing substantially drip-free, convenient application of antiseptic compositions compared to the conventional techniques described above.

One of the challenges associated with using such skin antiseptic compositions is the need to sterilize the exterior of the applicator while minimizing potential byproducts that may be produced when the composition is exposed to sterilization compounds such as ethylene oxide gas. Reactive sterilants such as ethylene oxide may react with the active antimicrobial agent or with other components in the skin antiseptic composition, altering the potency or producing potentially toxic compounds.

To address this problem, various solutions have been proposed. For example, the ChloraPrep® applicator, provided by CareFusion, has the active skin antiseptic composition, containing chlorhexidine gluconate (CHG), stored in a breakable glass ampule inside the applicator device. In the ChloraPrep® applicator, the sealed glass ampule protects the CHG composition during the sterilization process from ethylene oxide penetration which could otherwise compromise the efficacy of the antiseptic composition. CareFusion has a number of patents and patent applications including: U.S. Pat. Nos. 5,772,346 and 5,752,363 and U.S. Application Publication No. 2012/003029. Each of these teach the use of a sealed glass ampule containing CHG inside a skin antiseptic applicator.

An alternative solution to this problem is to construct the applicator container walls with layers of materials that are functionally impermeable to ethylene oxide gas. For example, U.S. Application Publication No. 2001/0054562 to Petterson, teaches a sealed medical device with a barrier layer to prevent ethylene oxide penetration by having the applicator walls made of a laminate material having an inner layer of polyolefin, an intermediate layer of silicon oxide and an exterior layer of polyethylene. Similarly, U.S. Pat. No. 8,105,306, assigned to 3M, teaches a skin antiseptic applicator with a container having a first interior layer of a polyolefin material which is impermeable to the liquid and vapor phases, and a barrier layer of polyester adhered to the interior layer which is impermeable to gaseous ethylene oxide. In the 3M applicator, both layers are free of silicon oxide. Another example is U.S. Application Publication No. 2012/184929, assigned to 3M, which teaches a skin antiseptic applicator with a container having a first interior layer which is permeable to the liquid and vapor phases, an adhesive layer for adhering the barrier layer to the interior layer, and a barrier layer which is impermeable to gaseous ethylene oxide.

One recurring problem with such existing skin antiseptic applicators is that the solutions provided to minimize ethylene oxide penetration also add additional cost and complexity to the applicator devices. From a manufacturing perspective, it would be preferable to provide an applicator having a container wall with only one layer (e.g., a homogenous layer) of material, rather than requiring multiple different layers. In addition, to reduce costs and simplify manufacturing of these devices, it would be an improvement to provide an applicator with a single compartment containing the skin antiseptic composition, instead of multiple initially separated compartments, or a sealed glass ampule inside of the applicator container.

One of the challenges associated with these skin antiseptic applicators is that the CHG or similar antiseptic compositions are often not stable with dye components. It is desirable to have a dye of a skin contrasting color along with the skin antiseptic composition, because then the practitioner applying the skin antiseptic composition to the patient and other healthcare providers who subsequently interact with the patient can more readily see where the composition has been applied on the skin. One solution is to provide the CHG composition in a separate compartment from a dye composition. For example, the ChloraPrep® applicators have the CHG composition in a glass ampule and the dye composition is provided in the foam applicator head. In the ChloraPrep® applicator the CHG composition flows through the dye and mixes with the dye in the applicator head. Another example of a two chamber applicator is described in U.S. Pat. No. 8,348,537, assigned to Covidien, which teaches an applicator with side-by-side, initially separate chambers for housing an antiseptic composition in one chamber and a dye in the other chamber. In the Covidien applicator, the dye and the antiseptic composition mix just prior to reaching the applicator head.

One problem with such existing skin antiseptic applicators containing multiple compartments for housing the dye separate from the antiseptic composition is that a multi-chamber applicator increases costs and complexity in the manufacturing process. From a manufacturing perspective, it would be preferable to provide an applicator needing only one compartment. In addition, it is preferable from a use perspective to have the dye and the antiseptic composition as one composition, as then the practitioner does not have to worry about mixing the two compositions together prior to application, and it eliminates the possibility that the antiseptic composition might be delivered to the patient's skin without dye or without sufficient dye to readily indicate to the practitioner where the product has been applied.

In view of the current state of the art, there is a continuing need for improved applicator products.

BRIEF SUMMARY

In an embodiment, the present invention is directed to an applicator for applying a composition (e.g., an antiseptic composition, personal care composition, etc.), comprising a container body having a proximal end and a distal end wherein the container body has a frangible member positioned at the distal end of the container body wherein the applicator has a first position where the container body and frangible member are a unitary structure, and a second position where the frangible member is rotated relative to the rest of the container body about a longitudinal axis to break a weak point and release the composition in the container body, allowing the composition to flow out of the container body through at least one opening. In one embodiment of the invention, a user may start with the applicator in a first position where the container body and the frangible member are a unitary structure, move to a second position to break the frangible member by rotating the frangible member relative to the container body, and then immediately move to a third position where the alignment between the container body and the frangible member is similar as it was in the first position except now the frangible member is bent and/or broken away from the container body. The applicator may be used either in the second position or in the third position to apply the antimicrobial composition to the patient's skin. The applicator also includes an applicator head formed of at least one porous material, positioned adjacent the distal end of the container body and the frangible member, wherein the composition flows out of the container body through the opening and onto the applicator head.

Another embodiment is directed to an applicator for applying a composition comprising a container body having one or more walls formed of a single layer of material that is substantially impervious to ethylene oxide, wherein the container body has a proximal end and a distal end, wherein the container body has a frangible member positioned at the distal end of the container body. The composition applicator has a first position where the container body and frangible member are a unitary structure that forms a sealed applicator, and a second position, when the frangible member breaks away from the rest of the container body at a weak point therebetween, creating at least one opening to allow the composition to flow out of the container body. In the second position the frangible member is rotated relative to the rest of the container body about a longitudinal axis. The applicator further includes an applicator head formed of at least one porous material, positioned adjacent to the distal end of the container body and the frangible member. The composition flows out of the container body onto the applicator head.

Another embodiment is directed to an applicator for applying a composition, the applicator consisting essentially of a container body having a proximal end and a distal end, wherein the container body has a frangible member positioned at the distal end of the container body. The applicator has a first position where the container body and frangible member are a unitary structure that forms a sealed applicator, and a second position, when the frangible member breaks away from the rest of the container body at a weak point therebetween, creating at least one opening to allow the composition to flow out of the container body. The applicator further includes an applicator head (e.g., formed of a porous material), positioned adjacent to the distal end of the container body and the frangible member. The composition flows out of the container body onto the applicator head. An antiseptic composition is initially stored in the container body, and includes a dye or colorant and an active selected from the group consisting of an antimicrobial agent, an antiviral agent, an antiseptic agent, and any combinations thereof. Optionally, the container body may include a barrier layer thereon to minimize ethylene oxide penetration. Alternatively, the container body may have a barrier material on a portion of the exterior of the container body. The barrier material may be a single material or a combination of materials and may have a continuous or a discontinuous form covering less than 100% of the exterior surface area of the container body. Suitable examples of barrier materials may include, but are not limited to: a printed pattern coating (stripes, dots, company logos, etc.), a shrink label, an adhesive label or sticker, a sleeve, a band, or other suitable alternatives.

Another embodiment is directed to a composition applicator comprising a container body having a proximal end and a distal end wherein the container body has a frangible member positioned at the distal end of the container body wherein the applicator has a first position where the container body and frangible member are a unitary structure, and a second position where the frangible member is broken away from the container body at a weak point therebetween and the frangible member is rotated out of alignment with the container body. The container body may include a sterile, aseptic composition provided therein, where the aseptic composition flows out of the container body through one or more openings created when the applicator is in the second position. The applicator also includes an applicator head formed of at least one porous material, positioned adjacent the distal end of the container body, wherein the composition flows out of the container body through the opening and onto the applicator head.

Another embodiment is directed to a composition applicator comprising a container body having one or more walls formed of a single layer of material that is substantially impervious to ethylene oxide, wherein the container body has a proximal end and a distal end, wherein the container body has a frangible member positioned at the distal end of the container body. The applicator has a first position where the container body and frangible member are a unitary structure that forms a sealed applicator, and a second position, when the frangible member breaks away from the rest of the container body at a weak point therebetween, creating at least one opening to allow the composition to flow out of the container body. In one embodiment, at least 60% of the surface area of the container body consists of a single layer of material, and the container body exhibits permeability to gaseous ethylene oxide of 20 mg/hr/cm$^2$, or less. The applicator further includes an applicator head formed of at least one porous material, positioned adjacent to the distal end of the container body and the frangible member. During use, once the frangible member is broken away, the composition flows out of the container body onto the applicator head.

Another embodiment is directed to a composition applicator comprising a container body having a proximal end and a distal end, wherein the container body has a frangible member positioned at the distal end of the container body. The composition applicator has a first position where the container body and frangible member are a unitary structure formed of a single layer of material that is substantially translucent, and a second position, when the frangible member breaks away from the rest of the container body at a weak point therebetween, creating at least one opening to allow the composition to flow out of the container body. In some embodiments of the invention, the applicator may have a third position where the alignment between the container body and the frangible member is similar as it was in the first position except now the frangible member is bent and/or broken away from the container body. The applicator further includes an applicator head formed of at least one porous material, positioned adjacent to the distal end of the container body and the frangible member. During use, once the frangible member is broken away, the composition flows out of the container body onto the applicator head. An aseptic composition is provided within the container body, the aseptic composition comprising: (i) an active selected from the group consisting of an antimicrobial agent, an antiviral agent, an antiseptic, and any combination thereof; (ii) an alcohol; and (iii) a dye or colorant. The composition does not necessarily need to be aseptic. For an antimicrobial applicator, it may be preferred that the composition is aseptic, but it is not required. Whether the composition is aseptic will depend on the intended use of the applicator.

Another embodiment is directed to a method of making an aseptic applicator, the method comprising the steps of extruding a polymeric material, placing the extruded material into a blow mold, molding the extruded material by placing a blow pin into the neck of the extruded material using pressure to form the material into a container body shape, filling the container body using the blow pin with an aseptic composition comprising an antimicrobial agent, an alcohol, and a dye or colorant, retracting the blow pin to create a frangible member and sealing the filled container body, and attaching a porous applicator head to the unitary structure to form the aseptic applicator. The frangible member attached to the distal end of the container body and the container body itself form a sealed, unitary structure.

Another embodiment is directed to a method of making an aseptic composition applicator, the method comprising the steps of (a) extruding a polymeric material; (b) placing the extruded material into a blow mold; (c) molding the extruded material by placing a blow pin into the neck of the extruded material using pressure to form the material into a container body shape; (d) using the blow pin, filling the container body with an aseptic composition comprising an antimicrobial agent, an alcohol, and a dye or colorant, (e) retracting the blow pin to create a frangible member attached to the distal end of the container body such that the container body and frangible member form a sealed, unitary structure, and sealing the filled container body using vacuum pressure; (f) attaching a porous applicator head to the unitary structure to form the aseptic applicator; and (g) sterilizing the aseptic applicator using ethylene oxide gas.

Another embodiment is directed to a method of making an aseptic applicator, the method comprising the steps of (a) extruding a polymeric material; (b) placing the extruded material into a blow mold; (c) molding the extruded material by placing a blow pin into the neck of the extruded material using pressure to form the material into a container body shape; (d) using the blow pin, filling the container body with an aseptic composition comprising an antimicrobial agent, an alcohol, and a dye or colorant, (e) retracting the blow pin to create a frangible member attached to the distal end of the container body such that the container body and frangible member form a sealed, unitary structure, and sealing the filled container body using vacuum pressure; (f) attaching a porous applicator head to the unitary structure to form the aseptic applicator; (g) sterilizing the aseptic applicator using ethylene oxide gas; and (h) packaging the sterilized aseptic applicator into an external packaging comprising at least one flexible portion.

Further features and advantages of the present invention will become apparent to those of ordinary skill in the art in view of the detailed description of preferred embodiments below.

BRIEF DESCRIPTION OF THE DRAWINGS

To further clarify the above and other advantages and features of the present invention, a more particular description of the invention will be rendered by reference to specific embodiments thereof which are illustrated in the drawings located in the specification. It is appreciated that these drawings depict only typical embodiments of the invention and are therefore not to be considered limiting of its scope. The invention will be described and explained with additional specificity and detail through the use of the accompanying drawings in which:

FIG. 5AA is a close up view of the distal end of the container body and frangible member of FIG. 5A;

DETAILED DESCRIPTION

I. Definitions

Figure 1A:
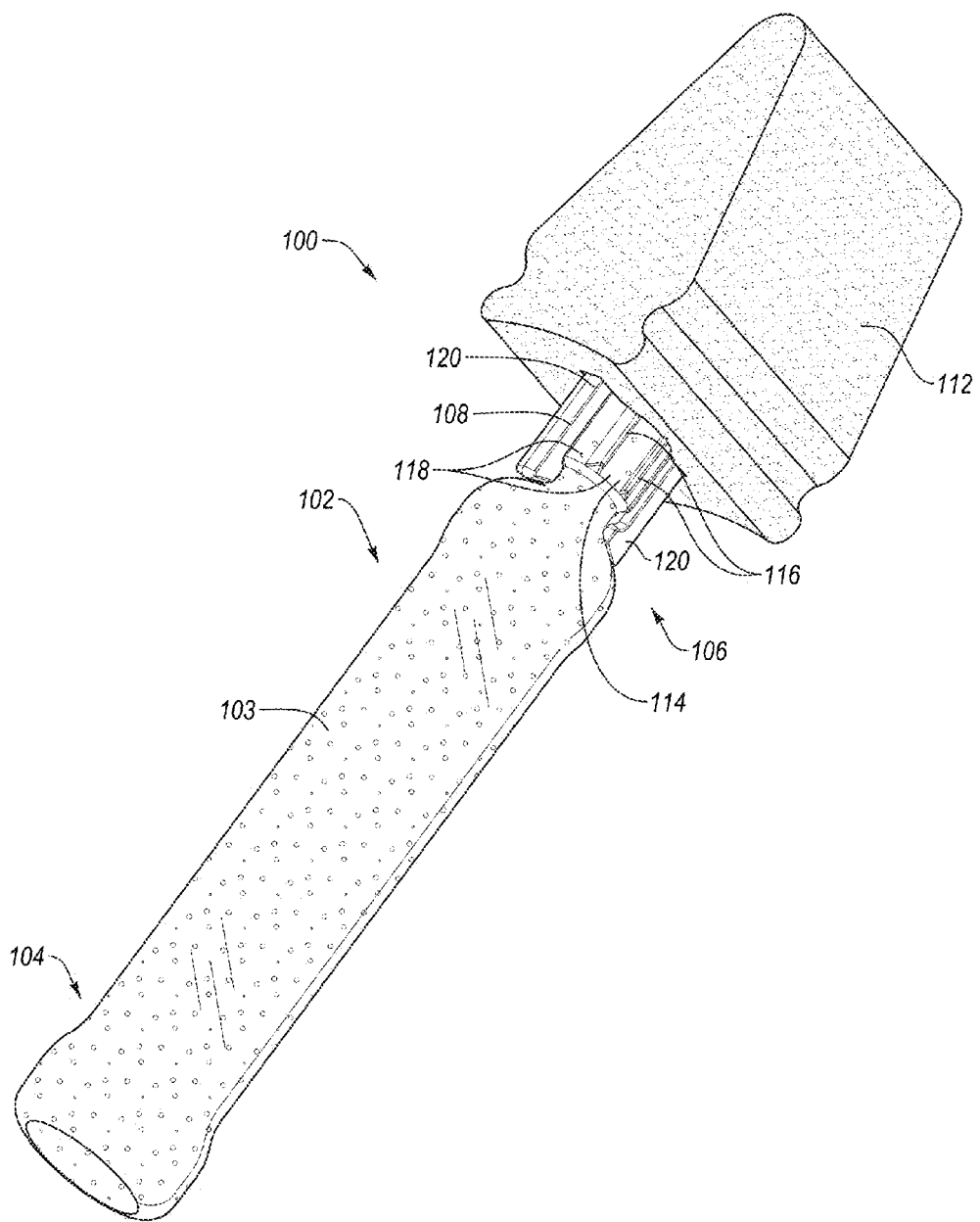
FIG. 1A is a perspective view showing an exemplary applicator according to the present invention.

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

The term "comprising" which is synonymous with "including," "containing," or "characterized by," is inclusive or open-ended and does not exclude additional, unrecited elements or method steps.

The term "consisting essentially of" limits the scope of a claim to the specified materials or steps "and those that do not materially affect the basic and novel characteristic(s)" of the claimed invention.

The term "consisting of" as used herein, excludes any element, step, or ingredient not specified in the claim.

It must be noted that, as used in this specification and the appended claims, the singular forms "a," "an" and "the" include plural referents unless the content clearly dictates otherwise. Thus, for example, reference to a "surfactant" includes one, two or more surfactants.

Various aspects of an antiseptic composition applicator may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present.

Various aspects of an antiseptic applicator may be illustrated with reference to one or more exemplary embodiments. As used herein, the term "exemplary" means "serving as an example, instance, or illustration," and should not necessarily be construed as preferred or advantageous over other embodiments of an antiseptic applicator disclosed herein.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In the application, effective amounts are generally those amounts listed as the ranges or levels of ingredients in the descriptions, which follow hereto. Unless otherwise stated, amounts listed in percentages ("wt %'s") are in wt % (based on 100 weight % active) of the particular material present in the referenced composition, any remaining percentage typically being water or an aqueous carrier sufficient to account for 100% of the composition, unless otherwise noted. For very low weight percentages, the term "ppm" corresponding to parts per million on a weight/weight basis may be used, noting that 1.0 wt % corresponds to 10,000 ppm.

II. Introduction

The present disclosure is directed to composition applicators and related methods of manufacture for providing antiseptic composition applicators that provide for prevention of contact between the practitioner and the skin of the patient, so as to avoid contamination. This may be accomplished by providing a container body to the applicator including a handle that may typically be about 4-6 inches long, with the handle oriented at an angle (e.g., 10-85 degrees) relative to the head of the applicator, through which head the composition is dispensed. The applicators include a frangible member that is initially a unitary structure with the remainder of the container body, providing a sealed compartment containing the composition that protects the composition during a sterilization process, and prevents the composition from flowing out of the applicator prematurely. The frangible member may be moved (e.g., rotated, bent, pulled away from, etc.) relative to the remainder of the container body, irreversibly breaking the seal, and providing an opening so that the composition can flow out of the container body through the opening, onto the porous applicator head, so as to allow delivery of the composition to the skin of the patient.

III. Exemplary Composition Applicators

The composition applicator may be compact and economically designed. As shown in FIGS. 1A-3A, a composition applicator 100 may comprise a substantially hollow container body 102, extending from a proximal gripping end 104 to a distal delivery end 106. A frangible member 108 may be positioned at distal end 106 of container body 102. As manufactured, container body 102 and frangible member 108 are initially a unitary structure, sealing a composition within hollow container body 102. This unitary configuration is referred to herein as a first position of the composition applicator. The composition applicator 100 further has a second position where the frangible member 108 is rotated relative to the remainder of container body 102 about longitudinal axis A to break a weak point (e.g., a region of narrowed cross-sectional thickness) 110 between frangible member 108 and the remainder of container body 102. Upon irreversible breakage, the composition within hollow container body 102 is free to flow out of body 102, through an opening at break point 110, and onto porous applicator head 112. Head 112 may comprise a porous, soft, readily deformable material (e.g., foam, nonwoven material, fabric, cotton swab, etc.) positioned adjacent distal end 106 of container body 102 and frangible member 108.

Figure 4A:
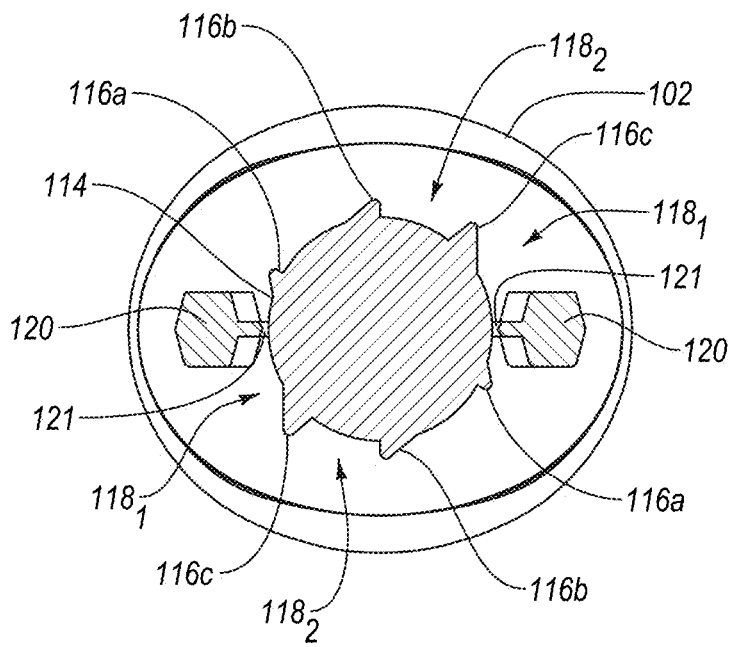
FIG. 4A is a cross-sectional view through the distal end of the container body, showing the frangible member in the first position relative to the container body.
Figure 4B:
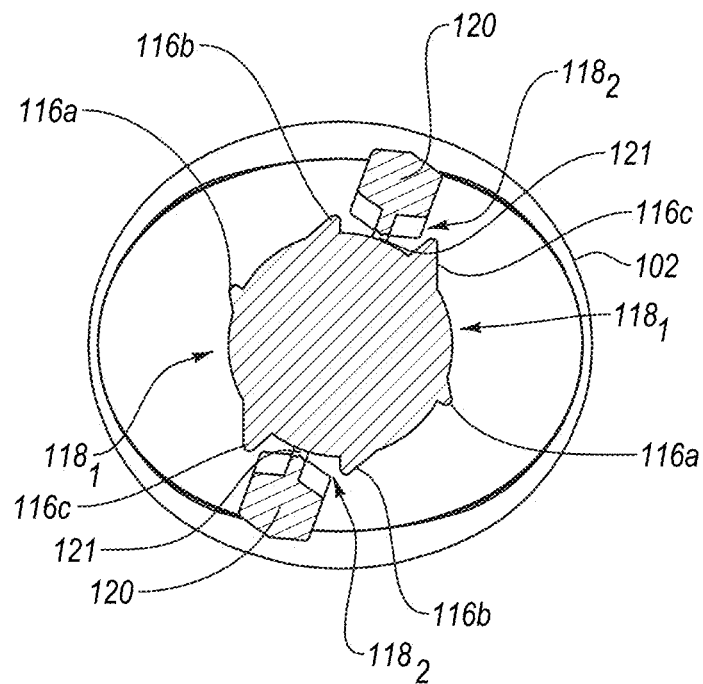
FIG. 4B is a cross-sectional view similar to that of FIG. 4A, but showing the frangible member in the second position, such that the weak point between the container body and frangible member has been broken, allowing composition in the container body to flow out the body through an opening and onto the applicator head.

Container body 102 may be of any desired shape (e.g., tubular in shape, cylindrical, triangular or oval cross-section, etc.). The container body 102 may include one or more compartments for housing the composition, or a component portion thereof. For example, liquids, gels and/or solids may be stored therein. Where multiple compartments are provided, they may be provided initially separate from one another, so as to allow mixing of the components from the various compartments just prior to use. The container body 102 may be elongate and tubular in shape. In one embodiment, the transverse cross-sectional shape of container body 102 may be circular, rounded, or oval. The Figures, particularly FIGS. 4A-4B show an oval cross-sectional shape. The container body 102 may have a transverse cross-section (e.g., as perhaps best seen in FIGS. 4A-4B) with an x-axis and a y-axis of unequal lengths. The end adjacent proximal end 104 is shown as generally flat, although it will be appreciated that in another embodiment the body 102 may have its sides sealed together at the proximal end 104, similar to a tube of toothpaste or antiseptic ointment.

In any case, the container body may be any suitable shape or size that can easily be grasped in one hand by a user. In an embodiment, the applicator may allow a practitioner to move between the first and second positions using only a single hand (e.g., by pressing head 112 against a surface, and twisting handle 103, while friction against the surface holds head 112 (and thus frangible member 108) stationary. In an embodiment, an external film, griping members or grip design (e.g., an elastomeric material overmolded on the handle portion 103 of container body 102) may be provided to aid the user in gripping and handling the applicator 100.

Figure 5A:
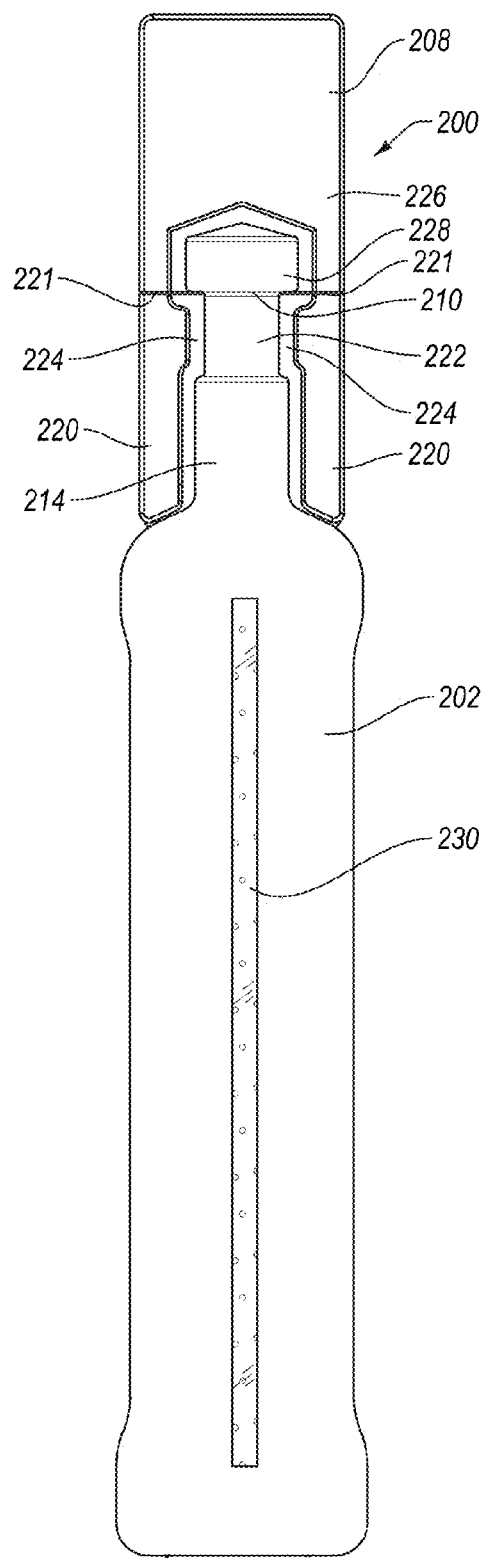
FIG. 5A is a perspective view of another exemplary applicator having an alternative configuration.
Figure 5A:
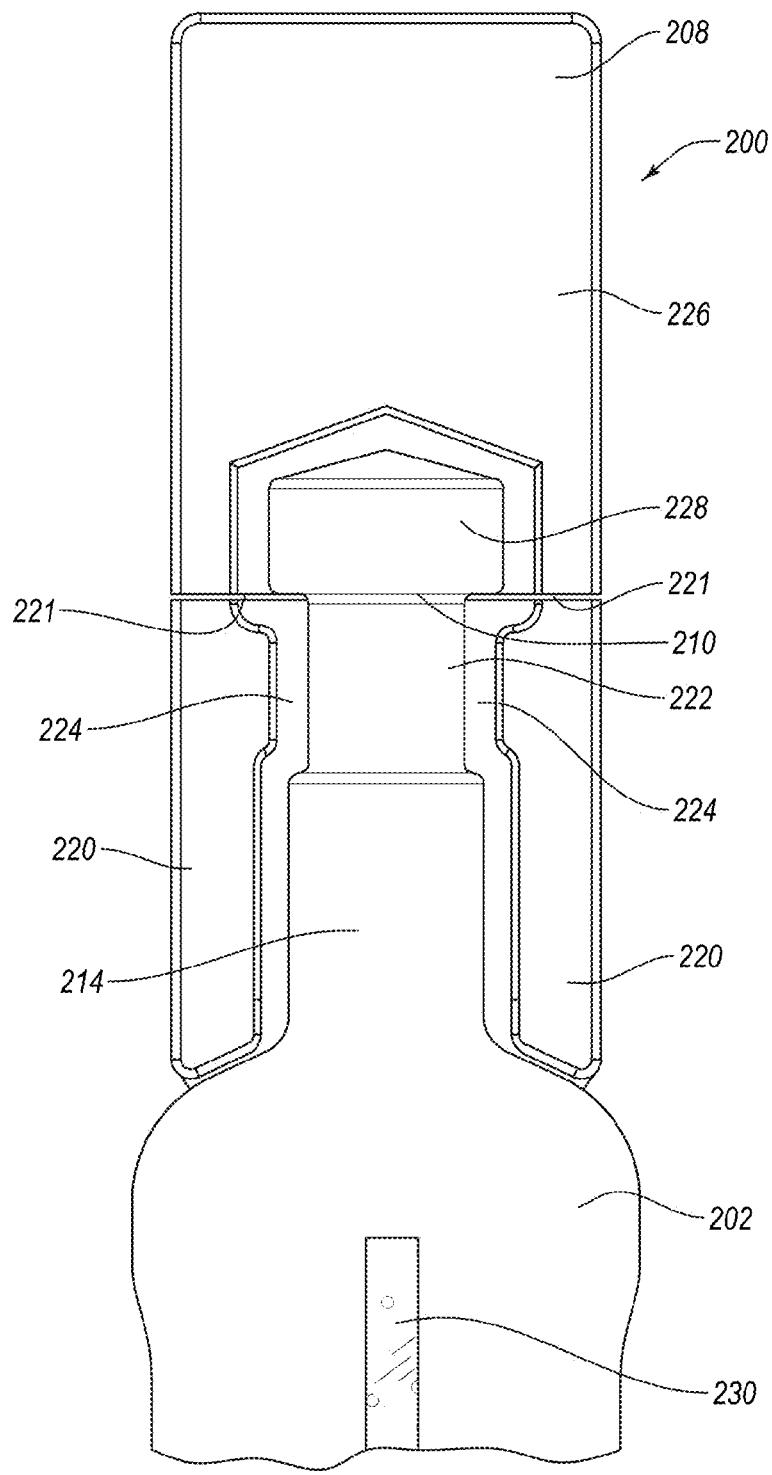

In an embodiment, the container body 102 may be symmetrical about longitudinal axis A. Along a latitudinal axis or transverse cross-sectioning plane, the container body 102 may include different shaped cross-sections at different points along the longitudinal axis of the container body. The container body 102 may include at least a portion thereof that can be seen through (e.g., transparent or translucent). Such a container body 102 may allow the practitioner to view the composition stored within hollow container body 102, e.g., allowing the practitioner to view the level of the composition within the applicator, as it is dispensed, and its level drops. In an embodiment, the entire container body may be formed of the same material (e.g., through a blow-fill-seal process). In another embodiment, container body 102 may include a window portion (e.g., an elongate viewing stripe) formed of such a transparent or translucent material. In such an embodiment, the remainder of container body 102 may be opaque. For example, it may include an inorganic oxide or colorant compounded with the polymeric material from which it is formed, or included as a discrete layer separate from the polymeric material. FIG. 5A shows such an otherwise opaque container body with a viewing window or elongate stripe.

Container body 102 may include one or more walls formed of a single layer of material, as may be provided through a blow-fill-seal process. The single layer of material may be substantially impervious to ethylene oxide (e.g., as used to sterilize the applicator). For example, the wall(s) of container body 102 may exhibit a permeability to gaseous ethylene oxide of 20 mg/hr/cm² or less. In an embodiment, the permeability may be such so that the composition contained within body 102 includes less than 250 ppm, less than 100 ppm, or less than 25 ppm of residual ethylene oxide (e.g., after sterilization).

Container body 102 may include a neck 114 at its distal end 106, adjacent frangible member 108. Neck 114 may include reduced dimensions relative to the handle portion 103 of body 102, and may include a different cross-sectional shape as compared to handle portion 103 of body 102. For example, while handle portion 103 is shown as being oval in cross-section, neck 114 may be generally circular. Neck 114 may include ramped protrusions 116 formed thereon which extend radially outward, so as to define a plurality of recesses 118 between adjacent protrusions 116 of neck 114. Wings 120 provided on frangible member 108 may be received within recesses 118, between protrusions 116, aiding in maintaining the applicator in the first or second position. For example, such a configuration may prevent inadvertent twisting and breakage of frangible member 108 relative to the remainder of container body 102 prematurely. In addition, once breakage of frangible member 108 has occurred, engagement provided between wings 120 and the appropriate corresponding recesses 118 defined between protrusions 116 may aid in maintaining the applicator in the second position (e.g., with frangible member 108 rotated relative to the remainder of container body 102.

Figure 1B:
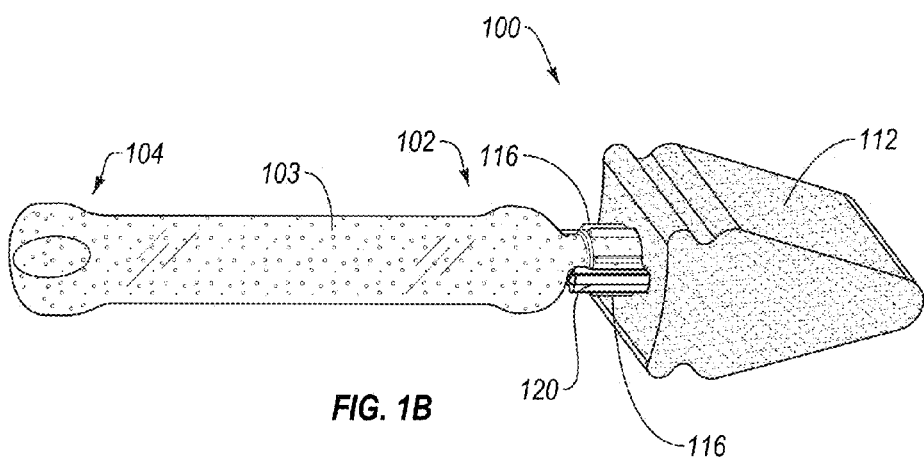
FIGS. 1B and 1C are side perspective view of the applicator of FIG. 1A, showing before and after activation, respectively.
Figure 1C:
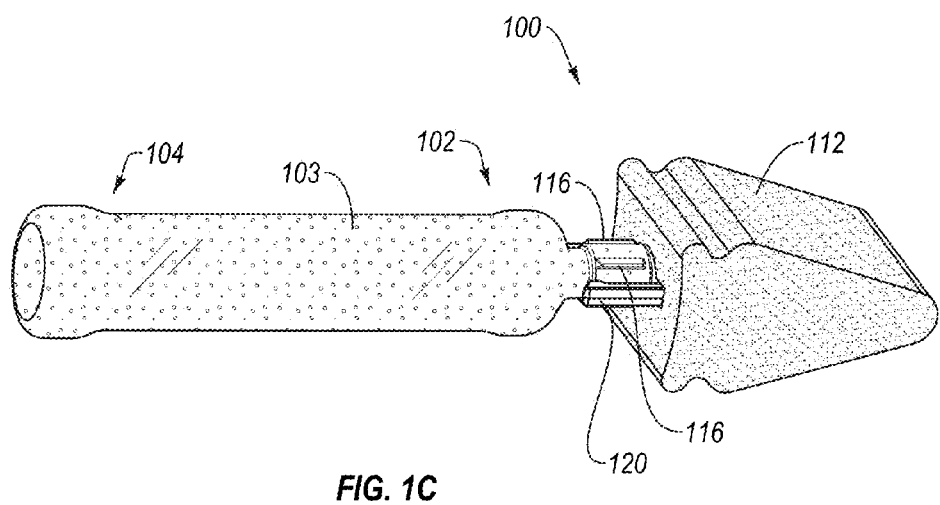
Figure 2:
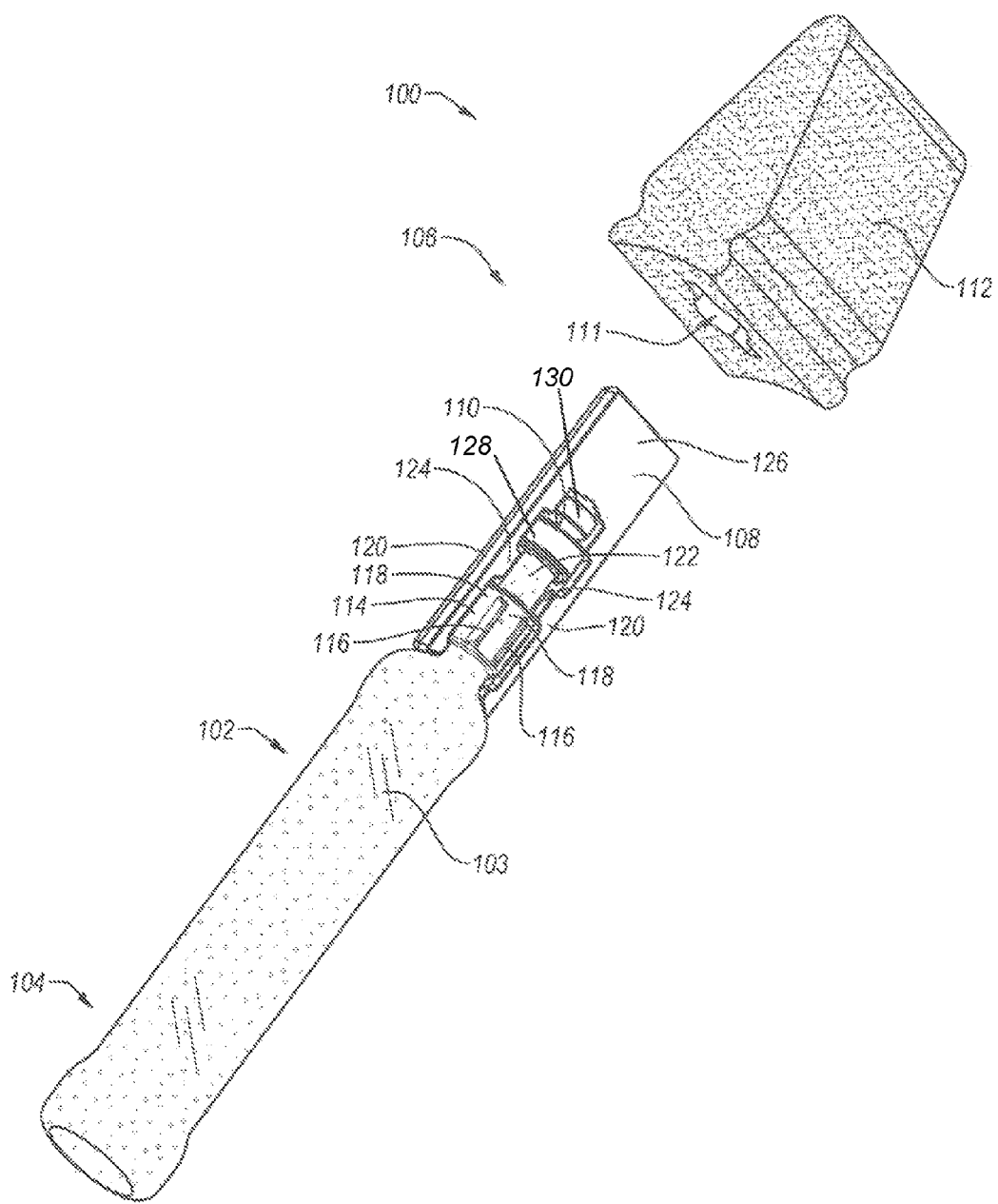
FIG. 2 is an exploded view of the applicator of FIG. 1A.

FIG. 1A shows applicator 100 with handle portion 103 of container body 102 and frangible member 108 in the first position, prior to fracture of a weak point 110 sealing the composition within body 102. Like FIG. 1A, FIG. 1B shows applicator 100 prior to activation. FIG. 1C shows applicator 100 with handle portion 103 and frangible member 108 in the second position, after fracture, allowing the composition within body 102 to flow out onto porous head 112. FIGS. 4A-4B (also showing views before and after fracture, respectively) perhaps best illustrate the geometry of the protrusions 116, corresponding recesses 118, and wings 120 of frangible member 108 that are received therein. As seen in FIGS. 1A-1B, in the first position, the long axis of the oval transverse cross-section of body 102 through handle portion 103 may be generally "horizontal", relative to the flat, horizontal surface provided by a bottom of foam head 112. As seen in FIG. 1C, the long axis of the oval transverse cross-section of body 102 through handle portion 103 may be generally "vertical" relative to the flat, generally horizontal surface at the bottom of foam head 112 (e.g., which would contact the patient's skin during use).

Figure 3:
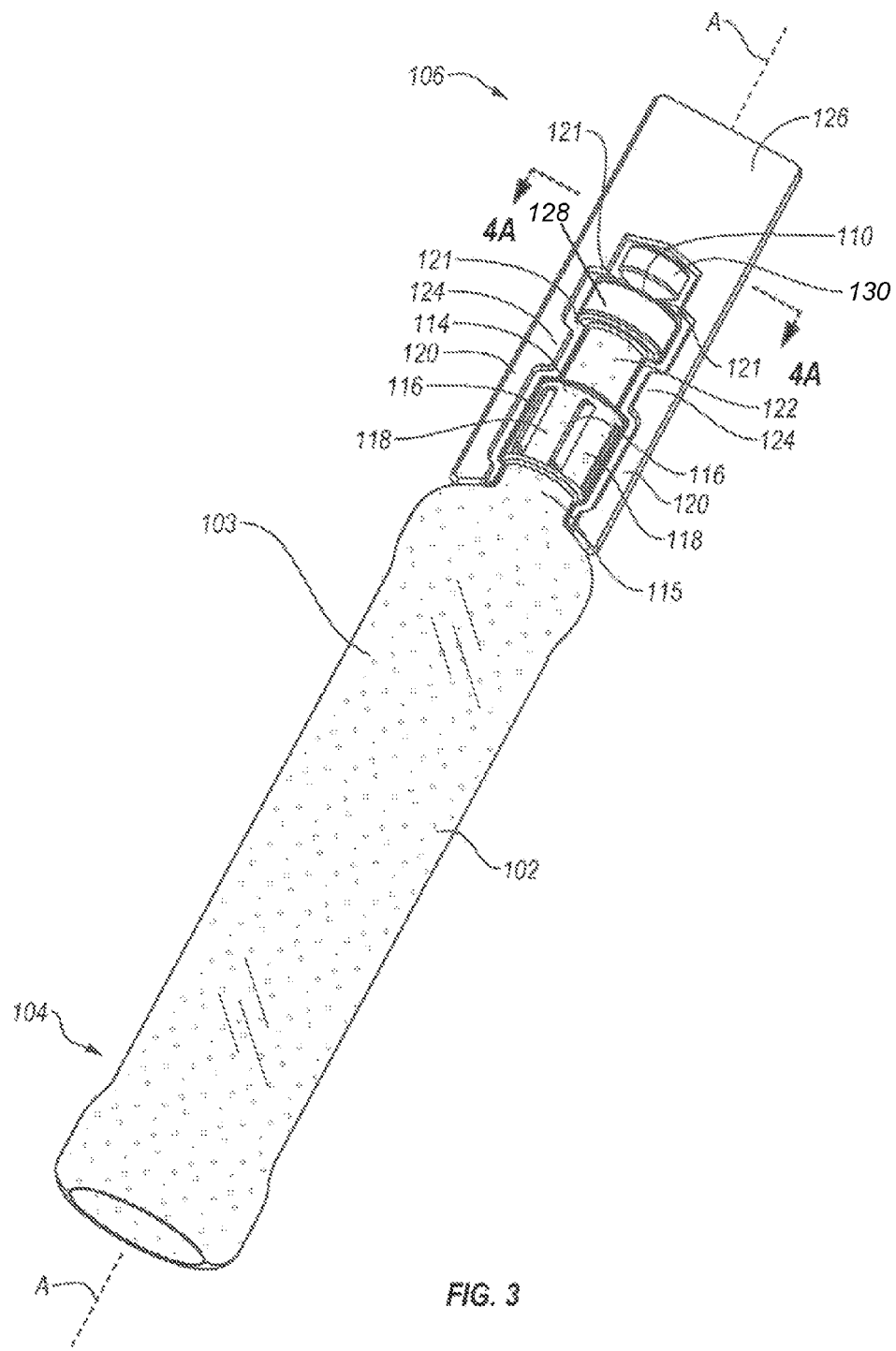
FIG. 3 is a perspective view of the applicator of FIG. 1A, in a first position, prior to breaking of a weak point between the frangible member and the container body, shown with the porous applicator head removed to more clearly illustrate the container body and frangible member.
Figure 3A:
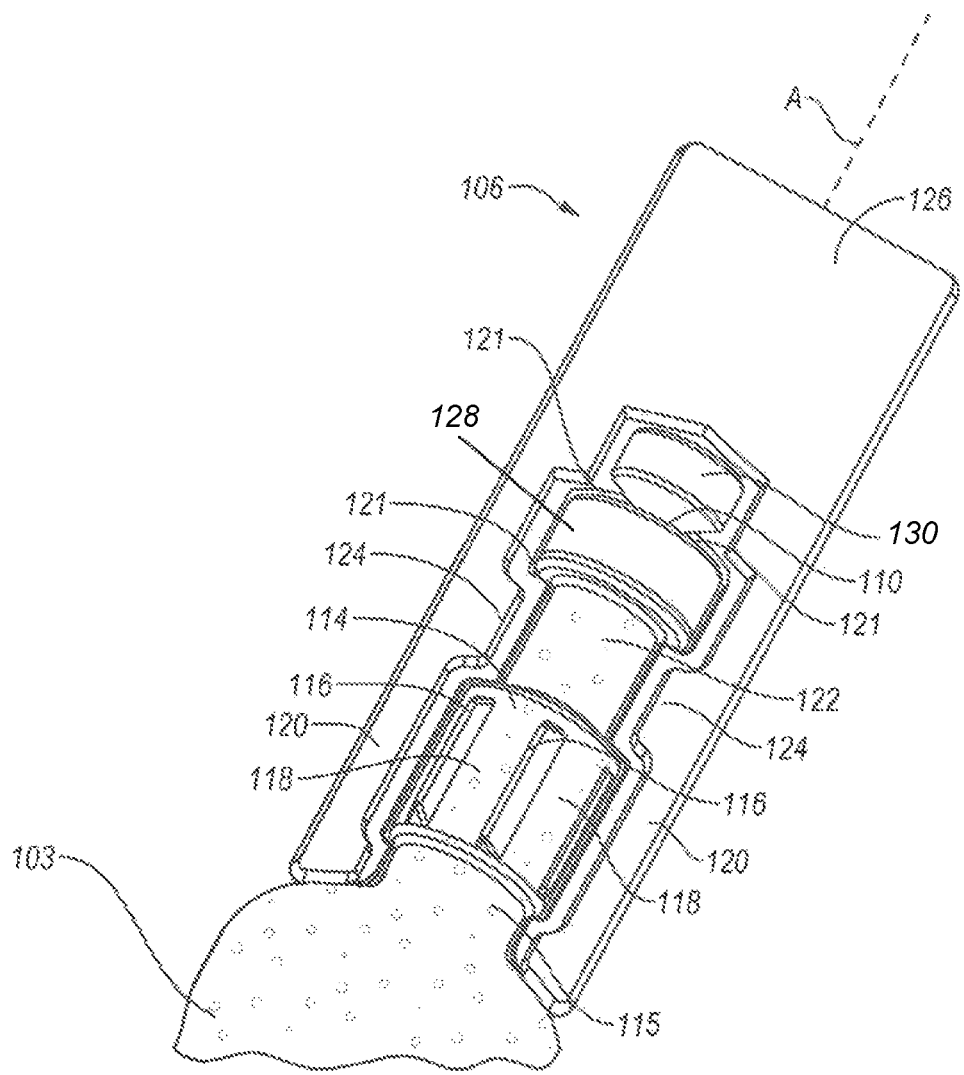
FIG. 3A is a close up view of the applicator of FIG. 3, showing the frangible member and distal end of the container body.

FIG. 4A shows the frangible member 108 and remainder of container body 102 in the first position, that of FIG. 3. FIG. 4B shows frangible member 108 having been rotated relative to the remainder of body 102, about longitudinal axis A, causing breakage of weak point 110, so as to allow initiation of flow of the composition within hollow body 102. As seen in FIG. 4A, wings 120 initially (in the first position) reside within recess $118_1$, defined between protrusions 116c and 116a. Referring to FIG. 4A, frangible member 108 may be rotated in a clockwise direction about neck 114 of container body 102, over first protrusion 116a, and into the recess defined between protrusions 116a and 116b. Further clockwise rotation of wing 120 (and frangible member 120) over second protrusion 116b, into recess $118_2$, is sufficient to irreversibly fracture weak point 110, permitting flow of the composition out of initially sealed container 102. FIG. 4B shows the second position, once frangible member 108 and wings 120 have been rotated, so that wings 120 reside within recesses $118_2$.

Protrusions 116 (e.g., 116a-116c) may be progressively larger than one another, so that protrusion 116c includes a lateral extension from neck 114 that is greater than the extension of protrusion 116b, and the extension of protrusion 116b is greater than that of protrusion 116a (i.e., extension of 116c>116b>116a). As is apparent from FIG. 4A, two of each protrusion may be provided, each set of protrusions 116a-116c corresponding to one of wings 120, as frangible member is rotated about neck 114 to break weak point 110. In addition to the progressively increasing lateral extension of the protrusions 116, the protrusions 116 may provide a ramped leading edge angle to facilitate wing 120 riding over protrusions 116a and 116b, but stopping against protrusion 116c.

For example, the leading edge angle of protrusion 116a over which wing 120 rides may be greater than 90°, so as to provide some initial threshold resistance against rotation over protrusion 116a, but still allow such rotation, when desired. In an embodiment, the leading edge angle of protrusion 116a may be from about 135° to about 175°, from about 140° to about 170°, or from about 145° to about 165° (i.e., presenting an incline to wing 120 of about 5° to about 45°, 10° to about 40°, or from about 15° to about 35°). The leading edge angle of protrusion 116b may be within similar ranges. The leading edge angle provided by protrusion 116c may be much steeper, so as to act as a stop against further rotation of frangible member 108. For example, the leading edge angle provided by protrusion 116c may be from about 70° to about 105°, from about 75° to about 105°, or about 80° to about 105° (i.e., presenting an incline to wing 120 of about 75° to about 110°, about 75° to about 105°, or about 75° to about 100°).

Lateral extension of wing 116c may be about 50% to about 100% more than protrusion 116b, and about 200% to about 300% more than protrusion 116a, as the lateral extension of the protrusions are progressively larger, "proud", or more prominent than one another. As a result of the increased lateral extension and the increasingly steep incline presented to wing 120 by protrusions 116, a minimum threshold force is needed to initiate breakage of frangible member 108, while also providing a stop to prevent further rotation of wing 120, once the second position where frangible member 108 is broken, has been assumed. While the configuration shown includes 3 different sets of protrusions for each wing, it will be appreciated that fewer or more may be provided. For example, a configuration may only include first and third protrusions 116a and 116c, respectively, the protrusion 116a serving to require a threshold amount of force to ride thereover so as to get out of the first position, and protrusion 116c serving as a stop to prevent rotation past the second position.

Distal to neck 114, an undercut portion 122 in the distal end 106 of container body 102 may be provided. In the illustrated embodiment, undercut portion 122 is positioned between neck 114 and the opening formed at weak point 110 upon breakage of weak point 110. Frangible member 108 may further be provided with one or more protrusions 124, which correspond to undercut portion 122 and extend inwardly (e.g., towards axis A) so as to be received within the undercut laterally adjacent to portion 122. Reception of protrusions 124 within the undercut adjacent portion 122 prevents up and down (proximal-distal) movement of frangible member 108 relative to the remainder of container body 102, even after assuming the second position, where frangible member has been broken relative to the remainder of body 102, so that member 108 and the remainder of body 102 are no longer a unitary structure. Of course, porous head 112 may also aid in retaining frangible member 108 in place, when in the second position.

As seen in FIGS. 4A and 4B, and described above in conjunction with FIGS. 1A-1C, in the first position, where container body includes an oval transverse cross-section through the handle portion 103, the oval may be oriented so that the longer axis of the oval is generally horizontal in the first position. Upon rotation and breakage of the weak point of the frangible member 108, the handle portion 103 has been rotated relative to the head 112 so that the longer axis of the oval is now generally vertical in the second position. For example, as seen, the rotation to move between the first and second positions may be about 80° to about 120°, or about 90° to about 110°. By providing the handle portion 103 with an oval cross-section, and providing the second position to correspond to a configuration where the head 112 remains as in the first position, but the handle portion 103 rotates so that the long axis of the oval is now generally vertical, the practitioner can readily determine which position the applicator is in. In addition, providing the second position with the oval's long axis in the generally vertical orientation facilitates improved gripping of the applicator in the hand of the practitioner, as compared to alternative orientations (e.g., with the long axis horizontal).

Head 112 may cover all or a portion of wings 120, protrusions 116, and recesses 118. For example, as shown in FIGS. 1A-1C, head 112 may extend proximally to a sufficient length to cover a portion of wings 120, protrusions 116, and recesses 118, while still allowing the most proximal portion of neck 114, protrusions 116, recesses 118, and wings 120 to be seen during use. Being able to see such structures may aid the practitioner in knowing how far frangible member 108 has been rotated relative to the remainder of body 102, and visually ascertaining whether the second position in which weak point 110 has been broken is achieved. Of course, upon fracture of weak point 110, a tactile and/or audible indicator (e.g., a "crack" both felt and/or heard) may also be provided, as the weak point 110 breaks.

The coverage of frangible member 108 by head 112 may also serve to provide good engagement between head 112 and frangible member 108, so as to ensure that head 112 and frangible member 108 rotate together during movement from the first position to the second position. For example, in an embodiment, head 112 may cover at least 50% of the surface area of the frangible member. As shown, frangible member 108 may include a generally flat, rectangular distal flange portion 126, providing engagement with head 112. Head 112 may include a correspondingly shaped recess 111 into which flange 126 and other structures of the covered portion of frangible member 108 are received. Frangible member 108 may include proximally extending wings 120 adjacent neck 114, described above, and inwardly extending protrusions 124, each of which may be received, at least in part by covering applicator head 112.

In order to provide undercut portion 122 with undercuts at both proximal and distal ends, an enlarged cylindrical stop 128 may be provided distal to undercut portion 122. The distal top of stop 128 may include a conical taper towards weak point 110, and a sealing cap 130, also enlarged in transverse cross-section relative to weak point 110 may be provided atop stop 128, so that weak point 110 is defined between top 128 and sealing cap 130. In an embodiment, frangible member 108 may be attached to the remainder of container body 102 only at its distal end, e.g., flange 126 attached to sealing cap 130. The wings 120 extending proximally from flange 126 may not be connected directly to the adjacent structures of the remainder of container body 102 (e.g., wings 120 may include a small space or gap 121 between stop 128 and wings 120. This space or gap 121 may continue proximally, so that wings are near, but not attached to undercut portion 122, and neck 114. The close up illustration of FIG. 3A may best illustrate this gap 121. While wings 120 may ride over protrusions 116, they may not be attached thereto. As shown, the proximal end of wings 120 may extend to a neck 115 just proximal to neck 114, below or proximal to protrusions 116, extending inwardly into this undercut neck 115 defined between the oval bottle shape portion of container 102 and neck 114.

The large surface area and planar shape provided by flange 126 and elongate, proximally extending wings 120 provides a large area for engagement with a corresponding inside recess 111 of applicator head 112, to ensure that head and frangible member remain together, as twisting from the first to the second position occurs, preventing frangible member 108 from "slipping" inside head 112 as twisting and breakage of the weak point is achieved.

Applicator head 112 may be attached to body 102 by any suitable means, including, but not limited to a snap fit, adhesive, friction fit, tabs or undercuts in the plastic body to hold the porous head 112 in place, hook and loop, screw on, etc. Porous applicator head 112 may be formed of a wide variety of materials, including but not limited to foam, sponge, non-woven fibrous substrates, woven fibrous substrates, etc. The porous material may be selected to provide a desired soak rate, or may be provided with structure features (e.g., slits, apertures, channels, differing foam density within portions of head 112, foam cell characteristics, etc.) to direct and control flow of the composition through applicator head 112.

Container body 102 may contain an aseptic composition therein. The composition may comprise a dye or colorant to provide a color (e.g., red, purple, green, etc.) to the composition so as to contrast against the skin to which the composition is to be applied. The composition may also include an active selected from the group consisting of an antimicrobial agent, an antiviral agent, an antiseptic agent, and any combinations thereof. By way of example, the active included in the composition is not particularly limited, and may be chlorhexidine, or a chlorhexidine salt, such as chlorhexidine gluconate. Other actives (e.g., povidone iodine (PVP-I), iodine, or other iodine complexes may also be used, as well as any other antimicrobial agents. An alcohol may also be included (e.g., methanol, ethanol, isopropyl alcohol, butyl alcohol, combinations thereof, etc.). The composition may be a liquid. In some embodiments, liquid components may mix with solid, gel, or other liquid components to result in a flowable liquid composition.

The composition contained within the body 102 may be aseptic, meaning it is generally sterile, so as to be free from disease causing contaminants (e.g., bacteria, viruses, fungi, parasites, etc.). The aseptic condition may be achieved through manufacture within a controlled environment, where contaminants are controlled, as well as through sterilization of the applicator once manufactured (e.g., through exposure to ethylene oxide gas). As will be apparent from the above, the composition may also be an antiseptic composition, where an antiseptic agent is included therein, so as to allow its application to skin so as to kill microbes, reducing the possibility of infection. Thus, the composition may be aseptic, and also antiseptic.

A barrier material acting as a barrier to ethylene oxide may optionally be provided on container body 102, so as to further limit ethylene oxide penetration through body 102, if desired. In an embodiment, no such separate barrier layer is provided, but rather the body 102 comprises a single layer of material. In such an embodiment, a barrier material may be incorporated into the single layer of material (e.g., compounded into the polymeric material from which the body 102 is formed). An example of such a barrier material is an inorganic oxide, such as a metal oxide. In another embodiment, a separate distinct layer of such an inorganic oxide barrier material may be provided.

The container body 102 and frangible member 108 may be formed from the same unitary piece of material (i.e., simple, one-piece design). In an embodiment, it is desirable to minimize the number of separate parts (e.g., a unitary container body/frangible member and an applicator head). Examples of suitable polymeric materials from which the container body 102 and frangible member 108 may be formed include, but are not limited to polyolefins, polypropylene, polyethylene (e.g., high density polyethylene, low density polyethylene), ethylene/propylene copolymers, ethylene/butylene copolymers, vinyl and vinyl polymers, acrylic polymers, polyesters (e.g., polyethylene terephthalate (PET), polybutylene terephthalate), polyvinyl alcohol, polyamides, polyvinylchloride, polyvinylidene chloride, ethylene vinyl alcohol, and any combinations or mixtures thereof. Fluorinated polymers, or layers may be employed, such as chlorotrifluoroethylene, polytetrafluoroethylene (PTFE), chlorotriflouroethylene, polyvinylidene fluoride, copolymers of perfluorinated monomers with partially fluorinated monomers such as copolymers of tetraflouroethylene/hexafluoropropylene/vinylidene (e.g., THV fluorothermoplastic from Dyneon Co.), and combinations thereof. In an embodiment, a blend of HDPE and polyamide may be employed to form a single layer container body.

Inorganic oxides (e.g., metal oxides) may be incorporated into any suitable polymeric material, as a barrier material, to decrease permeability of the resulting material to ethylene oxide penetration. In another embodiment, such a barrier material may be present as a separate, distinct layer (on the outside or inside of a polymeric wall layer, or sandwiched between various layers (e.g., between two polymeric wall layers). In another embodiment, the walls of the container body 102 may be substantially free of metal oxides (e.g., not intentionally added). Exemplary inorganic oxides include, but are not limited to silicon oxide, aluminum oxide, zinc oxide, magnesium oxide, and combinations thereof.

The polymeric material from which container body 102 is formed may be flexible, so as to deform under pressure (e.g., as applied by the hand of a practitioner squeezing handle 103). By blow molding container 102 of a polymeric material having such flexibility characteristics, and an appropriate wall thickness, such flexibility, deformability, and the ability to dispense the composition by squeezing handle portion 103 of body 102 may advantageously be provided. The walls of container 102 may exhibit sufficient strength so as to minimize and/or prevent undesirable stress-fracturing of the container (e.g., handle portion 103) due to repeated squeezing and releasing of the bottle shaped handle portion 103. A blow-fill-seal procedure may provide such benefits, as compared to, for example, thermoforming.

Figure 5B:
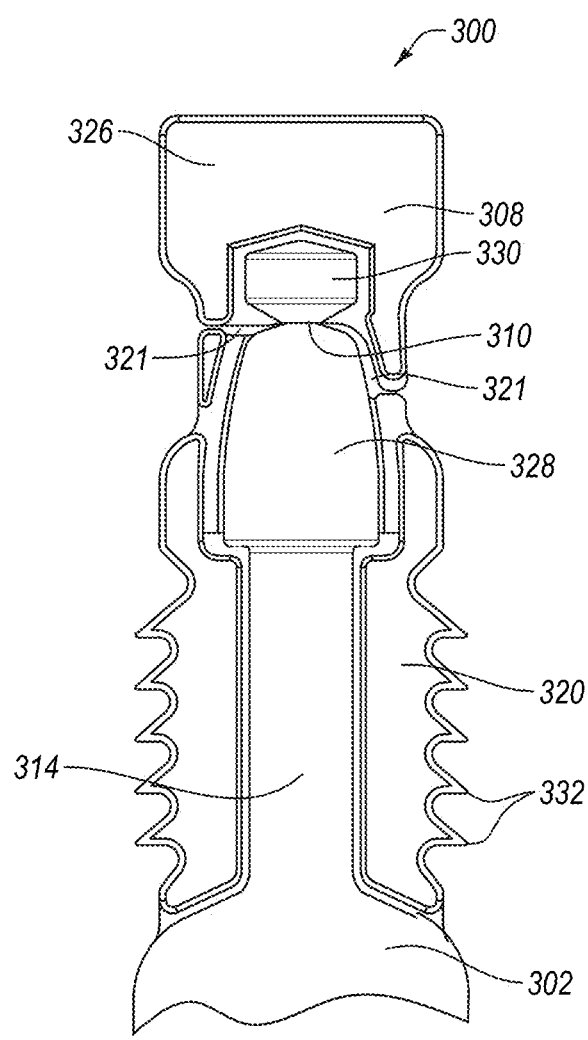
FIG. 5B is a perspective view of the distal end of another exemplary applicator having an alternative configuration.

FIGS. 5A and 5B illustrate additional alternative embodiments of exemplary applicators. FIG. 5A shows an applicator 200 similar to applicator 100, but with a differently configured frangible member 208 and surrounding distal portions of container body 202. In applicator 200, wings 220, including protrusions 224 may be attached to neck 214 and undercut portion 222, respectively, with a gap 221 between flange top portion 226 and wings 220. In one embodiment, no protrusions such as protrusions 116 and corresponding recesses 118 of applicator 100 may be present. N an alternative embodiment, protrusions such as 116 and corresponding recesses like 118 may be present but they would be positioned on the surface of concial portion 228. The protrusions would provide a tactile or auditory cue to the user to indicate how far they needed to rotate the frangible member to activate the applicator and release the composition. Unlike the protusions 116 and corresponding recesses 118 shown in FIGS. 3 and 3A, the protrusions for the embodiment in FIGS. 5A, 5AA and 5B should have an angle of about 135° to about 175° on either side so as to allow the user to rotate over the protrusion and back again in order to activate the applicator. Rather, only flange top portion 226, including conical portion 228, capping weak point 210 may twist relative to the remainder of body 202. FIG. 5A also illustrates an alternative body 202 at the grippable handle portion, e.g., including a container body 202 that may be opaque, except for at viewing window or stripe 230. FIG. 5AA shows a close up of the distal end of applicator 200, more clearly showing gap 221.

FIG. 5B shows another applicator 300, similar to applicator 100, but with a differently configured frangible member 308 and surrounding distal portions of container body 302. As in applicator 200, only the top portion 326 of applicator may twist during breaking. For example, wings 320 may be attached to neck 314, and remain therewith as the top flange 326 is broken off with sealing cap 330 by twisting rotation relative to enlarged stop 328 and the remainder of container body 302. Such action opens a fluid pathway from container body 302 through broken weak point 310, and into an attached porous head. A gap 321 may be present between top portion 326 and wings 320, to facilitate breakage at weak point 310. Wings 320 are shown as including barbed lateral extensions 332, which may further aid in retaining the distal end of container body 302 within a corresponding recess 111 of a porous head 112. In an alternative embodiment, the barbs may also be present on the top portion 326 of the applicator.

IV. Methods of Manufacture

The applicator may be manufactured using a blow-fill-seal process, which may be particularly beneficial, as a single apparatus or machine may be used to form and fill the applicator, all in a single process. Such a single process provides improved sterility as compared to a process requiring multiple machines (e.g., one to form the container, another to fill the container, and possibly another to seal the container). By forming the container, immediately filling the container, and immediately sealing the container, such an integrated blow-fill-seal process provides a sealed container, all within a short period of time, with no waiting or storage of intermediate manufactures, while the process is completed. For example, such a process includes less opportunity for contamination to occur as compared to forming the containers, after which the formed containers may be stored for a lengthy period of time, followed by retrieving containers from storage, filling the containers, and then sealing the containers. The sealed containers formed by such an integrated blow-fill-seal process may be sterilized, as needed (e.g., thermal sterilization, chemical sterilization (ethylene oxide, ozone, etc.), sterilization by radiation (gamma, electron beam, UV, etc.) and other suitable sterilization techniques) and have the porous applicator head attached over the distal end of the filled container. Placement of the applicator head 112 may occur prior to or after any ethylene oxide or similar sterilization step.

Because of the improvement in sterility offered by an integrated blow-fill-seal process, the sterilizing process may not need to be as rigorous as would otherwise be required. For example, lower ethylene oxide concentrations and/or exposure times may be suitable, while still providing a given level of sterilization. This may reduce ethylene oxide penetration into the composition, through the container body 102, which has heretofore been a recurring problem. For example, as a result, a single layer of polymeric material, with or without a barrier material compounded therein may be sufficient to meet the above described ethylene oxide penetration standards (e.g., less than 250 ppm, less than 100 ppm, less than 25 ppm of residual ethylene oxide within the composition). Similarly, where lower ethylene oxide concentrations and/or contact times may be suitable to achieve a given sterility level, the container body may be able to exhibit a permeability to gaseous ethylene oxide of greater than 20 mg/hr/cm$^2$ and still be able to meet the above described ppm levels of residual ethylene oxide in the composition. In an embodiment, at least 60% of the surface area of the container body may consist of a single layer of material. In an embodiment, the entire surface area of the container body may consist of a single layer of material.

Figure 6:
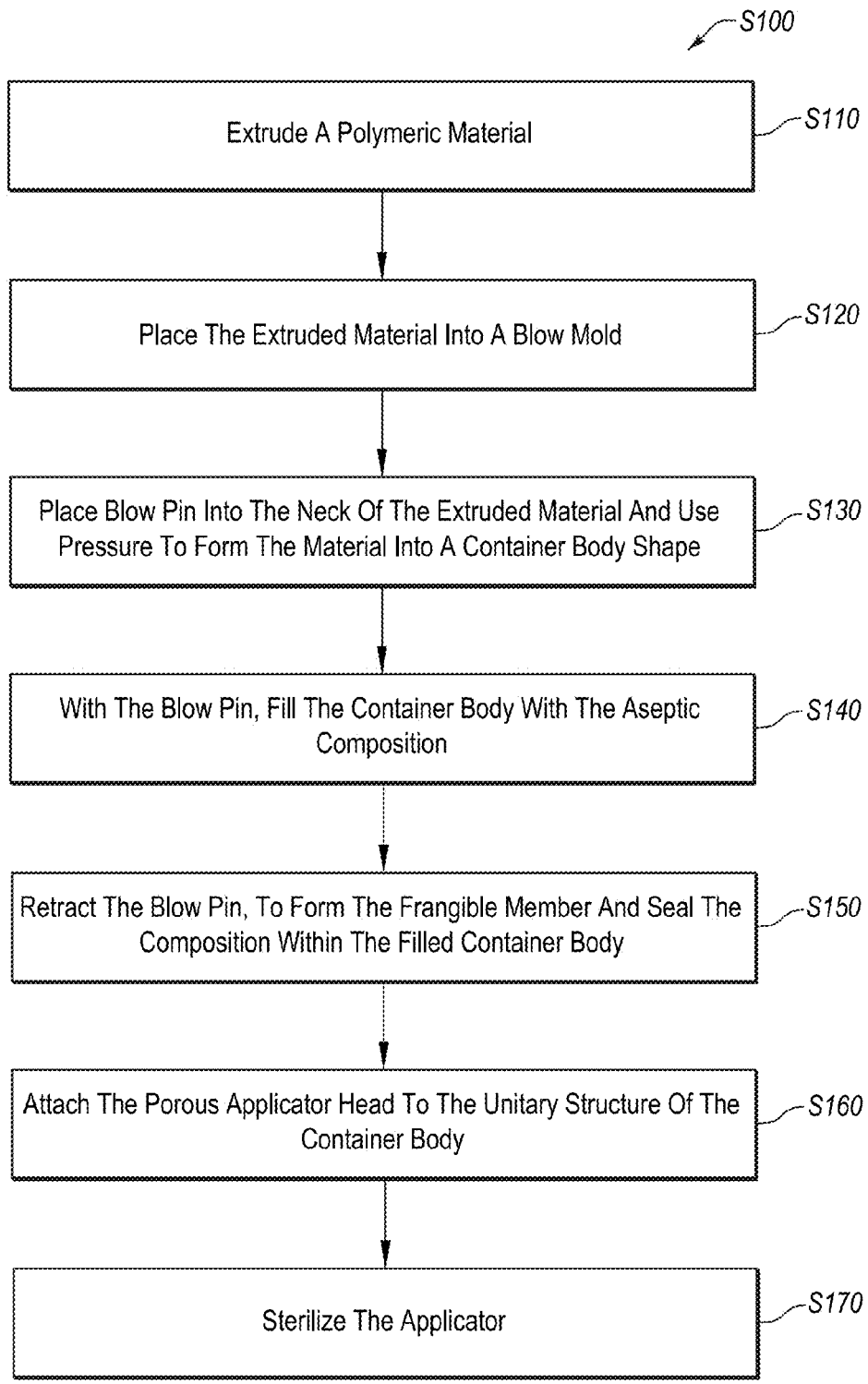
FIG. 6 is a flowchart illustrating an exemplary method according to the present invention.

FIG. 6 shows an exemplary method S100, including extruding a polymeric material at S110, placing the extruded material into a blow mold at S120, and at S130, molding the extruded material by placing a blow pin into the neck of the extruded material using pressure (e.g., provided through the blow pin) to form the material into a container body shape (e.g., container body 102). Pressure (e.g., from a compressed gas), or vacuum pressure may be used to mold the material into the desired container body shape. At S140, the container body is filled with the aseptic composition, which composition may comprise an alcohol, a dye or colorant, and an antimicrobial agent (e.g., antiseptic agent, antiviral agent, etc.). The composition may be introduced into the container body through the blow pin (e.g., the same blow pin used to form the polymeric material into a container body shape). Once the container body is filled, at S150, the blow pin may be retracted, which retraction results in the formation of a frangible member (e.g., frangible member 108, specifically weak point 110), sealing the composition within the filled container body. At S160, the porous applicator head (e.g., head 112) may be attached to the unitary structure of the container body (i.e., frangible member 108 and the remainder of body 102) to form the finished applicator. Steps S110 through S150 may be performed in sequence, all on the same blow-fill-seal apparatus.

Once formed, at step S170, the applicator may be sterilized (e.g., using ethylene oxide gas). Other sterilization techniques, e.g., sterilization by radiation (UV, gamma, electron beam, etc.), dry heat sterilization, steam sterilization, chemical sterilization (ethylene oxide, ozone, etc.) etc., may additionally or alternatively be employed.

Figure 7:
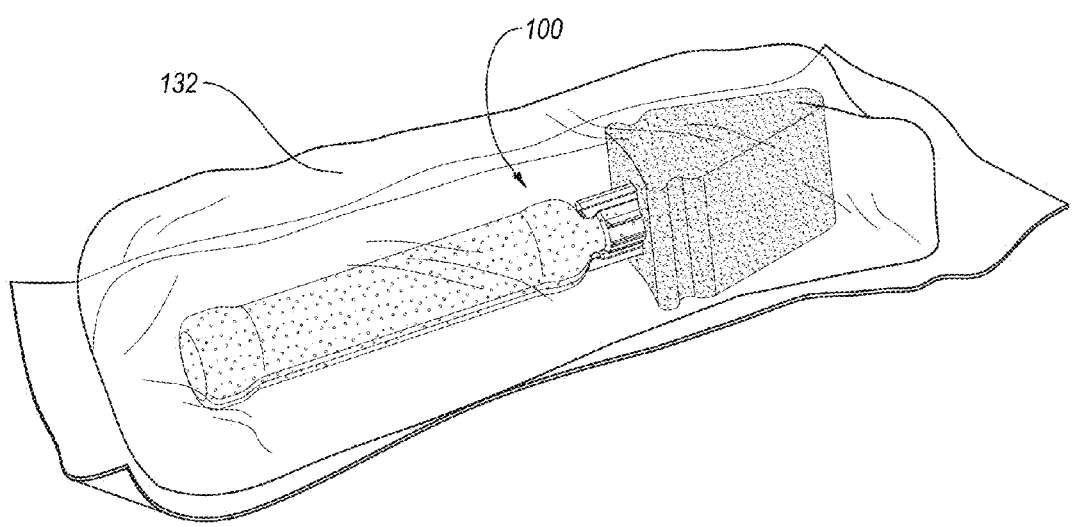
FIG. 7 shows the exemplary applicator of FIG. 1A in a sealed package.

Once sterilized, the applicator may be packaged into an external packaging material, e.g., comprising at least one flexible portion. FIG. 7 illustrates a sterilized applicator 100 packaged within packaging material 132, which material 132 includes at least one flexible portion. Such a package may be provided to the practitioner, and the practitioner may open the package, and use the applicator as described herein to apply the aseptic/antiseptic composition to the skin of a patient, e.g., by twisting head 112 (and frangible member 108) relative to the remainder of body 102 (e.g., handle 103), breaking weak point 110, so as to allow flow of composition out body 102, through an opening at broken weak point 110, and into head 112. By squeezing handle portion 103 of body 102, the practitioner may accelerate delivery of the composition over the flow path from body 102, out the opening at 110, soaking head 112, to the patient's skin. By providing at least a portion of body 102 with translucency or transparency, the practitioner may easily and readily visually ascertain how much composition remains to be dispensed.

Although described principally in the context of an applicator for applying an antiseptic composition, it will be appreciated that similar applicators (e.g., not necessarily including an applicator head) may be provided in other fields, e.g., for application of topical drugs, personal care compositions such as lotions, make-up, self-tanner, etc., paints, dyes, stains, glues, other adhesives, hard or soft surface cleaners, food marinates or flavors, etc.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

The invention claimed is:

1. A composition applicator comprising:
a container body having a proximal end and a distal end wherein the container body has a frangible member positioned at the distal end of the container body wherein the applicator has a first position where the container body and frangible member are a unitary structure and a second position when the frangible member is rotated relative to the rest of the container body about a longitudinal axis to break a weak point between the frangible member and the remainder of the container body and release the composition in said container body, allowing the composition to flow out of the container body through at least one opening; and
an applicator head formed of at least one porous material and positioned adjacent to the distal end of the container body and said frangible member wherein the composition flows out of the container body through said at least one opening onto the applicator head;
wherein said frangible member has one or more wings and said container body has a neck and an undercut between the neck and the at least one opening of the container body, the undercut aligning with one or more inwardly oriented protrusions on the one or more wings of the frangible member so that the frangible member does not move substantially axially relative to said container body in the second position.

2. The composition applicator of claim 1 wherein the longitudinal axis of the container body extends from the proximal end to the distal end and the container body is symmetrical about the longitudinal axis.

3. The composition applicator of claim 1 wherein said container body has substantially different shaped transverse cross-sections at different locations along the longitudinal axis of the container body.

4. The composition applicator of claim 1 wherein said container body has a substantially oval transverse cross-section in plan view.

5. The composition applicator of claim 1 wherein said container body has at least one translucent portion.

6. The composition applicator of claim 1 wherein said container body is formed of a translucent material.

7. The composition applicator of claim 1 wherein said container body is formed of a transparent material.

8. The composition applicator of claim 1, wherein said applicator head substantially covers said one or more wings.

9. The composition applicator of claim 1 wherein said neck has a first protrusion with a first leading edge angle to present an incline to the corresponding wing of about 5 degrees to about 45 degrees, and a second protrusion with a second leading edge angle to present an incline to the corresponding wing of about 75 degrees to about 110 degrees.

10. The composition applicator of claim 1, wherein each wing comprises two inwardly oriented projections.

11. The composition applicator of claim 1, wherein the container body neck comprises a plurality of radially outwardly extending ramped protrusion to engage the one or more wings as the frangible member is rotated relative to the rest of the container body.

12. A composition applicator comprising:
a container body having one or more walls formed of a single layer of material that is substantially impervious to ethylene oxide, wherein said container body has a proximal end and a distal end wherein the container body has a frangible member positioned at the distal end of the container body wherein the composition applicator has a first position where the container body and frangible member are a unitary structure that forms a sealed applicator and a second position when the frangible member is rotated and breaks away from the rest of the container body at a weak point creating at least one opening to allow the composition to flow out of the container body; and
an applicator head formed of at least one porous material and positioned adjacent to the distal end of the container body and said frangible member wherein the composition flows out of the container body onto the applicator head;
wherein the frangible member has at least one wing and the container body comprises a neck with at least one radially outwardly extending ramped protrusion that engages the wing as the frangible member is rotated relative to the rest of the container body.

13. The composition applicator of claim 12 wherein said container body has a transverse cross-section in plan view with an x-axis and a y-axis of unequal lengths.

14. The composition applicator of claim 12 wherein said walls are formed of a translucent material.

15. The composition applicator of claim 12 wherein said container body exhibits permeability to gaseous ethylene oxide of 20 mg/hr/cm$^2$ or less.

16. The composition applicator of claim 12 wherein said container body exhibits permeability to gaseous ethylene oxide so as to result in less than 250 ppm ethylene oxide residual in the composition.

17. The composition applicator of claim 12 wherein said container body exhibits permeability to gaseous ethylene oxide so as to result in less than 150 ppm ethylene oxide residual in the composition.

18. A composition applicator comprising:
a container body having a proximal end and a distal end wherein the container body has a frangible member positioned at the distal end of the container body wherein the composition applicator has a first position where the container body and frangible member are a unitary structure that forms a sealed applicator and a second position when the frangible member is rotated and breaks away from the rest of the container body at a weak point creating at least one opening to allow the composition to flow out of the container body;
an applicator head positioned adjacent to the distal end of the container body and said frangible member wherein the composition flows out of the container body onto the applicator head; and
an aseptic composition in said container body comprising a dye or colorant and an active selected from the group consisting of an antimicrobial agent, an antiviral agent, an antiseptic agent, and any combination thereof; and
wherein the frangible member has at least one wing and the container body comprises a neck with first and second radially outwardly extending protrusions forming a recess therebetween, the at least one wing being positioned in the recess when the frangible member is rotated to the second position.

19. The composition applicator of claim 18 wherein said second position is reached when the frangible member is rotated relative the rest of the container body about a longitudinal axis to break a seal thereof.

20. The composition applicator of claim 18, wherein said active is chlorhexidine gluconate.

21. The composition applicator of claim 18, wherein said container body and frangible member are formed of a single layer of polyolefins, polypropylene, polyethylene, high density polyethylene, low density polyethylene, ethylene/propylene copolymers, ethylene/butylene copolymers, vinyl, vinyl polymers, acrylic polymers, polyesters, polyethylene terephthalate, polybutylene terephthalate, polyvinyl alcohol, polyamides, polyvinylchloride, polyvinylidene chloride, ethylene vinyl alcohol, chlorotrifluoroethylene, polytetrafluoroethylene, chlorotriflouroethylene, polyvinylidene fluoride, copolymers of perfluorinated monomers with partially fluorinated monomers, tetraflouroethylene/hexafluoropropylene/vinylidene, or combinations thereof.

22. The composition applicator of claim 18, wherein said container body and frangible member are formed of a single layer of polymeric material, further comprising an inorganic oxide incorporated into the polymeric material from which the container body and frangible member are formed.

23. The composition applicator of claim 18, wherein a user of said applicator may move between the first position and the second position using only one hand.

24. The composition applicator of claim 18, wherein the at least one wing comprises a first wing and a second wing, and wherein the first protrusion has a first leading edge angle to present an incline to the first wing of about 5 degrees to about 45 degrees and the second protrusion has a second leading edge angle to present an incline to the second wing of about 75 degrees to about 110 degrees.

25. The composition applicator of claim 18, wherein the second protrusion is larger than the first protrusion.

26. The composition applicator of claim 18, wherein walls of the container body are substantially free of any metal oxides.

27. The composition applicator of claim 18 wherein at least 60% of the surface area of the container body consists of a single layer of material and wherein the container body is substantially impermeable to gaseous ethylene oxide so that less than 250 ppm of ethylene oxide penetrates into the composition in said applicator during sterilization.

28. The composition applicator of claim 18 wherein said container body includes a viewing stripe or window that is transparent or translucent while the remainder of the container body is opaque.

* * * * *